United States Patent
Singaram et al.

(10) Patent No.: US 10,274,483 B2
(45) Date of Patent: Apr. 30, 2019

(54) FLUORESCENCE METHOD FOR SENSING CHLORINATED DISACCHARIDES

(71) Applicant: THE REGENTS OF THE UNIVERSITY OF CALIFORNIA, Oakland, CA (US)

(72) Inventors: Bakthan Singaram, Oakland, CA (US); Angel Resendez, Oakland, CA (US); Dominic-Luc Webb, Oakland, CA (US)

(73) Assignee: THE REGENTS OF THE UNIVERSITY OF CALIFONIA, Oakland, CA (US)

( * ) Notice: Subject to any disclaimer, the term of this patent is extended or adjusted under 35 U.S.C. 154(b) by 115 days.

(21) Appl. No.: 15/316,503

(22) PCT Filed: Jun. 5, 2015

(86) PCT No.: PCT/US2015/034557
§ 371 (c)(1),
(2) Date: Dec. 5, 2016

(87) PCT Pub. No.: WO2015/188144
PCT Pub. Date: Dec. 10, 2015

(65) Prior Publication Data
US 2017/0184574 A1 Jun. 29, 2017

Related U.S. Application Data

(60) Provisional application No. 62/008,441, filed on Jun. 5, 2014.

(51) Int. Cl.
*G01N 33/53* (2006.01)
*C07F 5/02* (2006.01)
(Continued)

(52) U.S. Cl.
CPC .......... *G01N 33/5308* (2013.01); *C07F 5/025* (2013.01); *G01N 21/6428* (2013.01);
(Continued)

(58) Field of Classification Search
None
See application file for complete search history.

(56) References Cited

U.S. PATENT DOCUMENTS

2012/0208286 A1  8/2012  Gamsey et al.
2013/0121925 A1  5/2013  Singaram et al.

OTHER PUBLICATIONS

Anderson, A.D.G. et al. A simple method for the analysis of urinary sucralose for use in tests of intestinal permeability, Ann Clin Biochem vol. 42:, pp. 224-226 (Year: 2005).*
(Continued)

*Primary Examiner* — Xiaoyun R Xu
(74) *Attorney, Agent, or Firm* — Kilpatrick Townsend & Stockton LLP

(57) ABSTRACT

Disclosed are systems for measuring the concentration of a disaccharide in an aqueous medium, the system comprising a boronic acid derivative and a fluorescent molecule. Also disclosed are methods of determining gastrointestinal permeability in a subject, the method comprising contacting an aqueous medium obtained from a subject with the above system to obtain a mixture, where the patient has consumed a known quantity of a disaccharide; measuring the fluorescence emission of the mixture; and correlating the extent of fluorescence emission to the concentration of the disaccharide in the aqueous medium; and correlating the concentration of the disaccharide in the aqueous medium to the gastrointestinal permeability in the subject. Also disclosed are methods of determining the concentration of a disaccharide in an aqueous medium, the method comprising contacting the aqueous medium comprising the disaccharide with the above system to obtain a mixture; measuring the fluo-
(Continued)

rescence emission of the mixture; and correlating the extent of fluorescence emission to the concentration of the disaccharide in the aqueous medium.

8 Claims, 4 Drawing Sheets

(51) Int. Cl.
    *G01N 33/58*     (2006.01)
    *G01N 21/64*     (2006.01)

(52) U.S. Cl.
    CPC ... *G01N 33/582* (2013.01); *G01N 2021/6439* (2013.01); *G01N 2400/00* (2013.01); *G01N 2800/06* (2013.01); *G01N 2800/70* (2013.01)

(56) References Cited

OTHER PUBLICATIONS

Rooyakkers et al., "Simple and sensitive multi-sugar-probe gut permeability test by high-performance liquid chromatography with fluorescence labelling", J Chromatogr A. Apr. 12, 1996;730(1-2):99-105.
International Search Report and Written Opinion dated Sep. 23, 2016 in PCT/US2015/034557 (8 pages).
PCT/US2015/034557, International Search Report and Written Opinion dated Sep. 23, 2015, 7 pages.
Rooyakkers et al., "Simple and sensitive multi-sugar-probe gut permeability test by high-performance liquid chromatography with fluorescense labelling", Journal of Chromatography A, vol. 730, 1996, 99-105.

\* cited by examiner

FLUORESCENCE METHOD FOR SENSING CHLORINATED DISACCHARIDES

RELATED APPLICATIONS

The present invention is filed under 35 U.S.C. § 371 as the U.S. national phase of International Patent Application No. PCT/US2015/034557, filed Jun. 5, 2015, which designated the U.S. and claims priority to the U.S. Provisional Application Ser. No. 62/008,441, filed on Jun. 5, 2014, by Bakthan SINGARAM et al., and entitled "FLUORESCENCE METHOD FOR SENSING CHLORINATED DISACCHARIDES," the entire disclosure of each of which is incorporated by reference herein, including all the drawings.

FIELD OF THE INVENTION

The present invention is in the field of sensing molecules in solution, and in particular, a method for sensing and quantifying chlorinated disaccharides in solution.

BACKGROUND OF THE DISCLOSURE

Gastrointestinal barrier dysfunction is now recognized as an early event in the pathogenesis of several problematic diseases, such as inflammatory bowel disease (IBD), Parkinson's disease, Crohn's disease, celiac disease and type 1 and 2 diabetes mellitus. There is a critical need, both in clinics and research, for a way to efficiently map and quantify leaky regions of the gastrointestinal (GI) tract. Permeability testing is becoming one of the prominent ways of characterizing changes in small intestine histology, malabsorption of nutrients, and abnormal permeability of the intestinal mucosa. Gastrointestinal permeability can be assessed noninvasively by analyzing saccharide biomarkers in urine such as sucrose for upper GI permeability, lactulose and mannitol for small intestine permeability. The synthetic sweetener sucralose is the main probe of choice for colonic permeability. Current methods for analyzing these biomarkers require expensive and time consuming instrumentation such as high performance liquid chromatography/mass spectrometry (HPLC/MS).

Devices and methods for sensing glucose in solution are described elsewhere, for example in, U.S. Pat. Nos. 6,653,141, 6,627,177, 7,470,420, 7,968,714, and 8,394,357, and Patent Application Publication Nos. US 2004-0028612 A1, US 2009-0148956 A1, US 2012-0009126 A1, and US 2013-0121925 A1, the entire disclosure of all of which is incorporated by reference herein, including the drawings. However, these documents disclose the sensing of glucose, a monosaccharide. Further, chemical strategies for altering chlorinated sugar derivatives (e.g., sucralose) such that they can be detected and quantified are not described.

Thus, there is a need in the art for a low cost, high throughput urinalysis assay that will detect chlorinated saccharide biomarkers in urine. This would enable clinicians to immediately gain insight about microscopic tissue damage that cannot be seen by endoscopy.

SUMMARY OF THE INVENTION

Disclosed are systems for measuring the concentration of a disaccharide in an aqueous medium, the system comprising a boronic acid derivative and a fluorescent molecule. Also disclosed are methods of determining gastrointestinal permeability in a subject, the method comprising contacting an aqueous medium obtained from a subject with the above system to obtain a mixture, where the patient has consumed a known quantity of a disaccharide; measuring the fluorescence emission of the mixture; and correlating the extent of fluorescence emission to the concentration of the disaccharide in the aqueous medium; and correlating the concentration of the disaccharide in the aqueous medium to the gastrointestinal permeability in the subject. Also disclosed are methods of determining the concentration of a disaccharide in an aqueous medium, the method comprising contacting the aqueous medium comprising the disaccharide with the above system to obtain a mixture; measuring the fluorescence emission of the mixture; and correlating the extent of fluorescence emission to the concentration of the disaccharide in the aqueous medium.

DETAILED DESCRIPTION OF THE EMBODIMENTS

Figure 1:
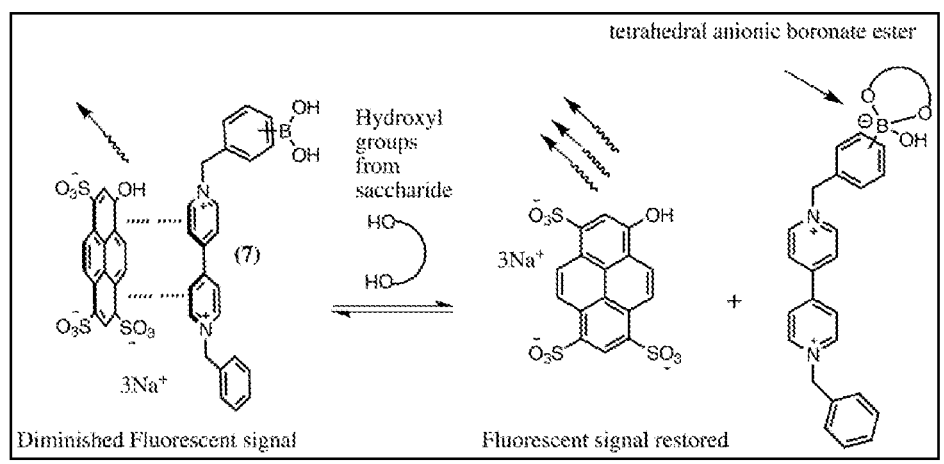
FIG. 1 is a schematic drawing showing the interaction between the two component fluorescent sensor system based on boronic acid appended bipyridinium salt oMBV (7) or ortho bis-boronic acid viologen (oBBV) as the receptor and corresponding HPTS reporter dye.

Provided herein are systems and methods for the measurement of gastrointestinal permeability in a subject. In broad terms, a subject is asked to consume a known quantity of a disaccharide, preferably a non-metabolizable disaccharide. After a certain amount of time, a fluid, for example urine, is obtained from the subject. The fluid is then contacted with a system having a fluorophore and a boronic acid derivative. Normally, the boronic acid derivative quenches the fluorescence of the fluorophore. When the disaccharide is present, the fluorophore binds the disaccharide and loses its ability to quench the fluorophore. The more disaccharide is present in the solution, the more fluorescent the solution is. By comparing the fluorescence obtained from an unknown sample, and comparing the fluorescence to a series of standards, the concentration of the disaccharide in the solution is determined. If one knows how much disaccharide was consumed, then one is able to measure the extent of the permeability of the gastrointestinal track.

Thus, disclosed herein are systems for measuring the concentration of a disaccharide in an aqueous medium, the system comprising a boronic acid derivative and a fluorescent molecule.

In some embodiments, the boronic acid derivative is a viologen derivative. In other embodiments, the boronic acid derivative is cationic. In certain embodiments, the boronic acid derivative has a core structure of a compound of Formula 1.

In certain embodiments, the boronic acid derivative is a compound selected from the group consisting of

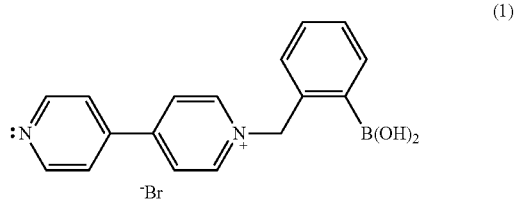

(1)

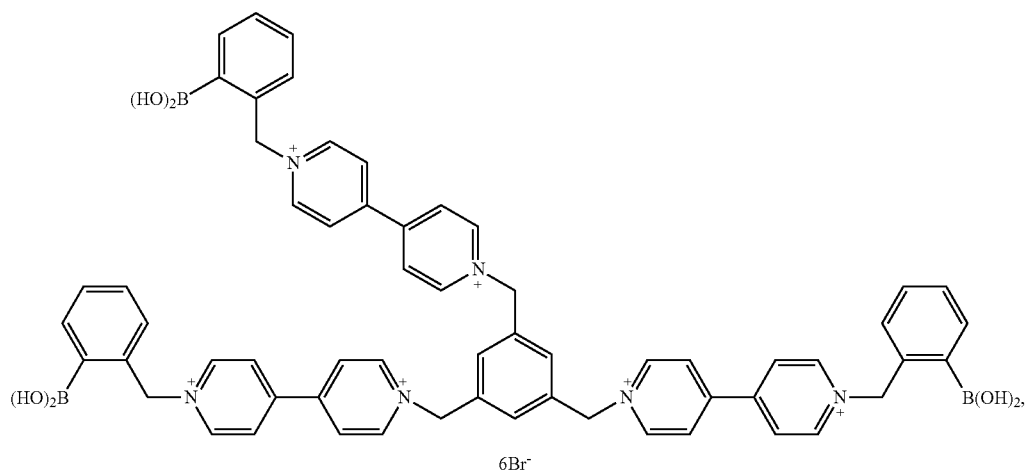

(5)

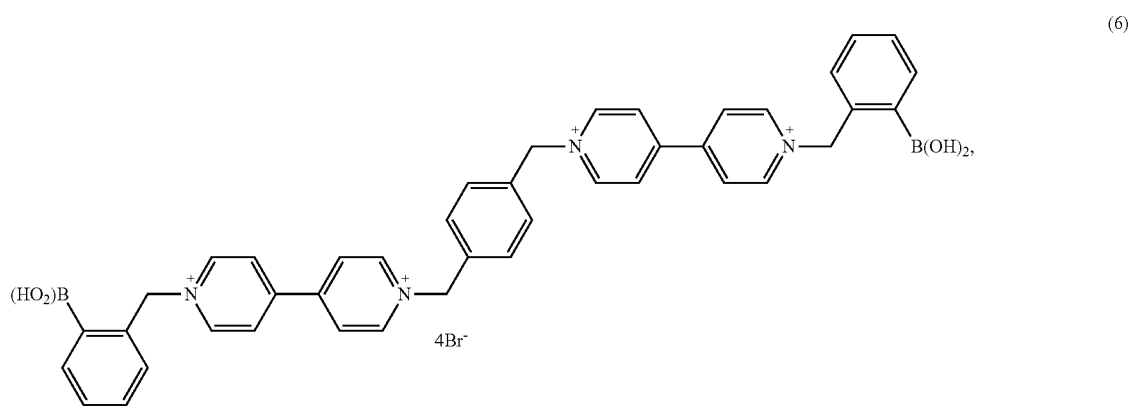

(6)

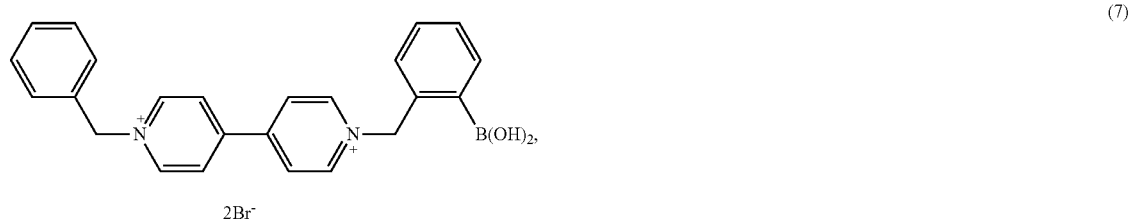

(7)

-continued
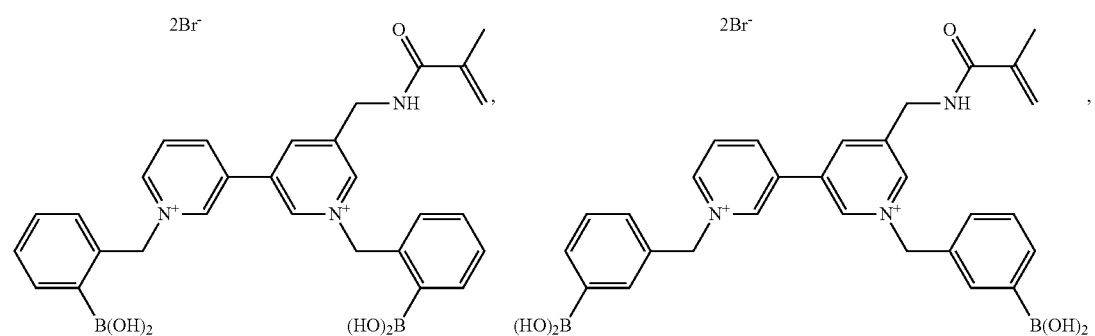
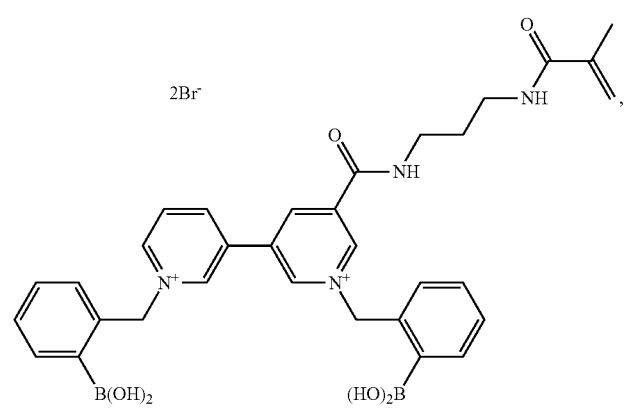
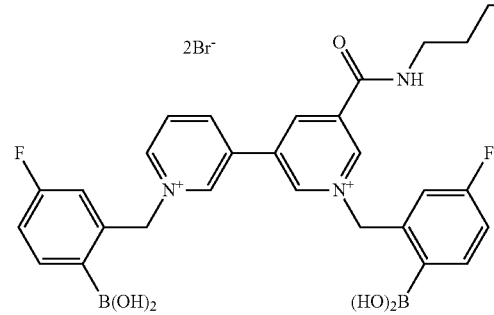
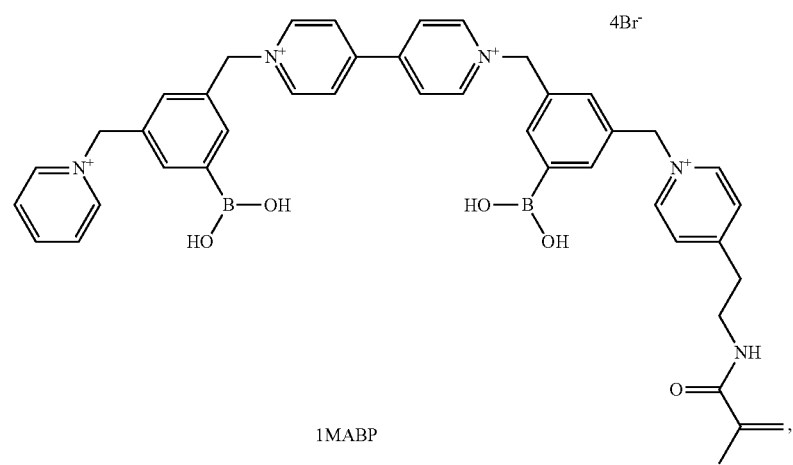
1MABP

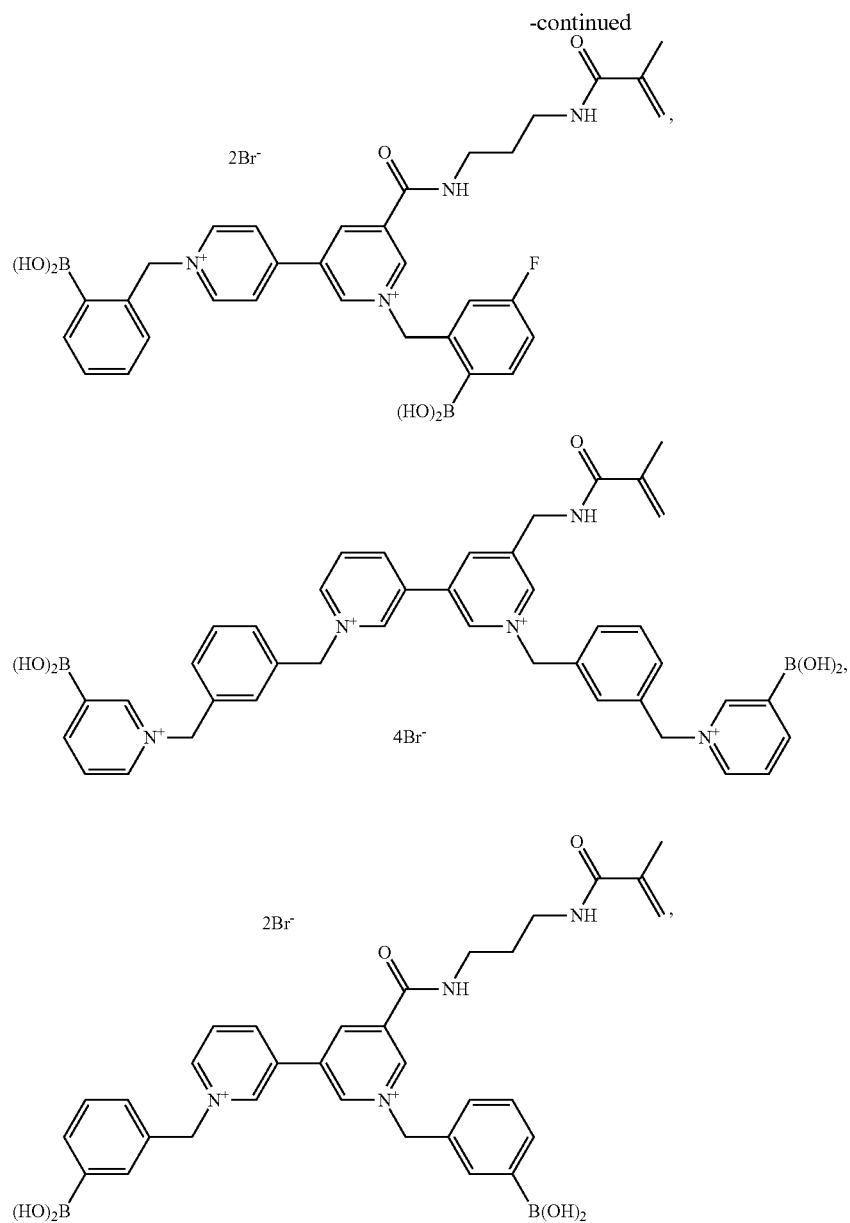
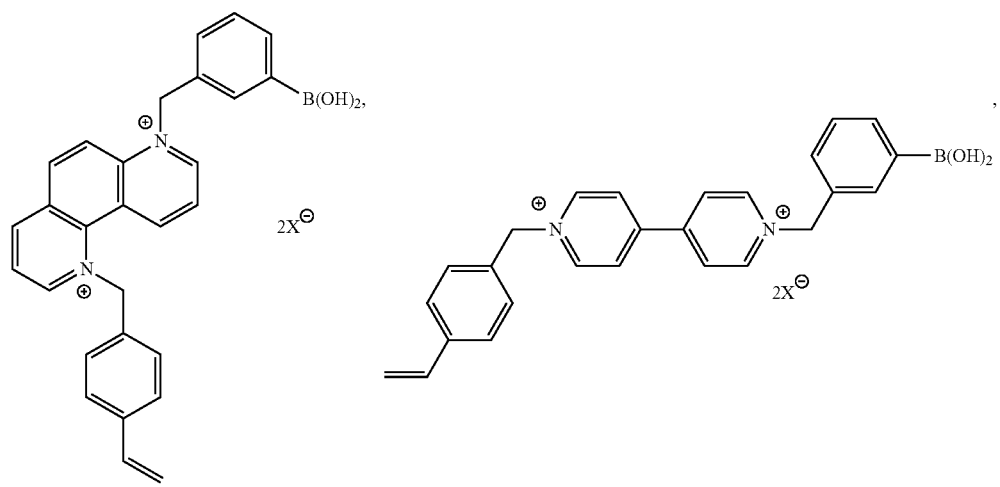

-continued
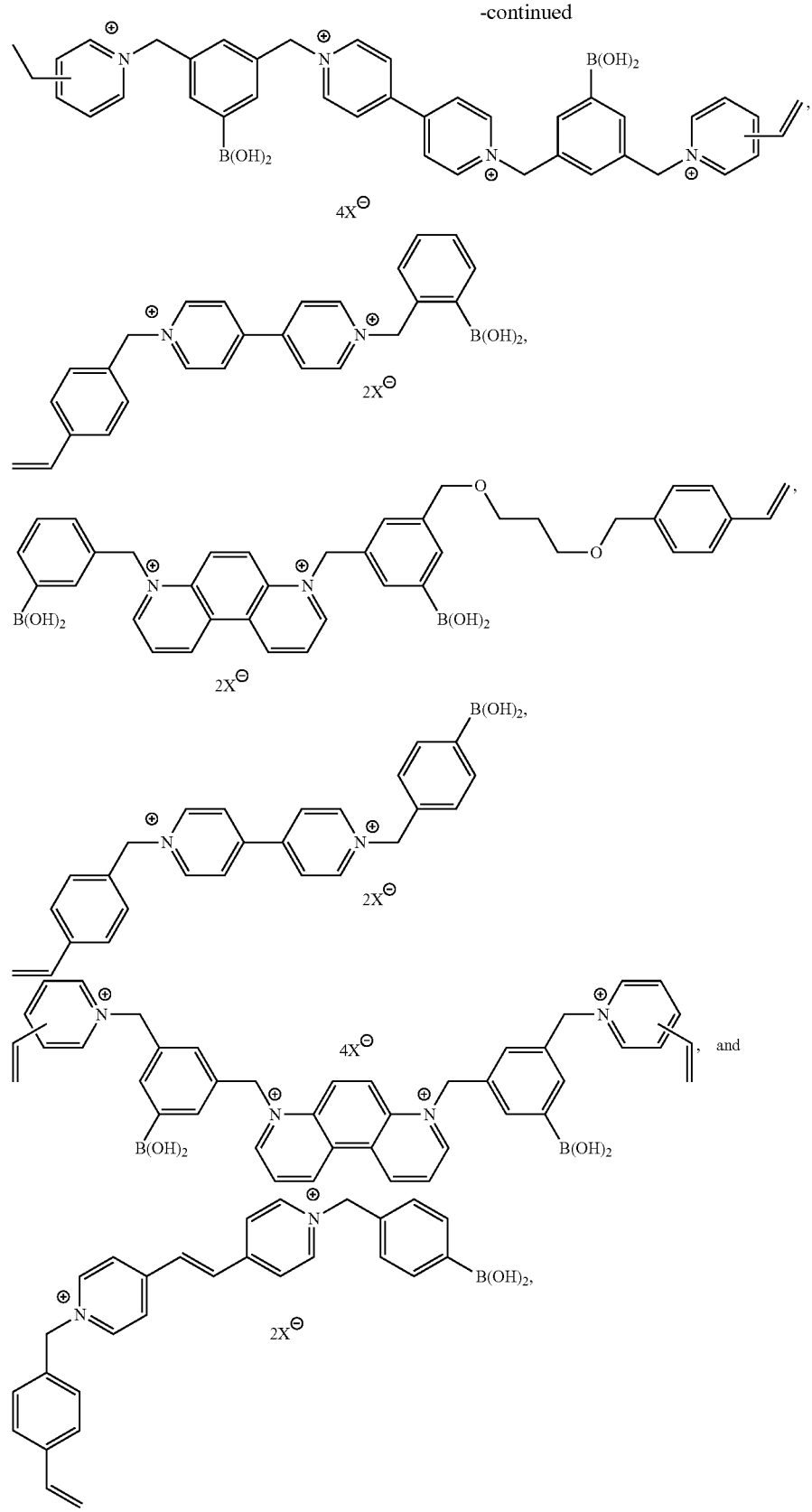
wherein X is bromide or chloride.

In some embodiments, the boronic acid derivative is a compound selected from the group consisting of trans-1,2-bis(4,4'-N,N'-(benzyl-4-boronic acid)-pyridinium)ethylene dibromide; 1,7-N,N'-bis(benzyl-3-boronic acid)-phenanthrolinium dibromide; benzyl viologen (BV)-a comparative quencher; 4,4'-N,N'-bis-(benzyl-2-boronic acid)-dipyridinium dibromide (oBBV); 4,4'-N,N'-bis-(benzyl-3-boronic acid)-dipyridinium dibromide (mBBV); 4,4'-N,N'-bis-(benzyl-4-boronic acid)-dipyridinium dibromide (pBBV); N,N'-bis (benzyl-(2, 3, or 4)-boronic acid-4,7-phenantholinium halide (4,7-phen-o, m, or p-BBV); 4-N-(benzyl-2-boronic acid)-4'-N'-(benzyl)-dipyridinium bromide chloride; 4-N-(benzyl-3-boronic acid)-4'-N'-(benzyl-4-ethenyl)-dipyridinium bromide chloride (m-SBBV); 4-N-(benzyl-2-boronic acid)-4'-N'-(benzyl-4-ethenyl)-dipyridinium bromide chloride (o-SBBV); 4-N-(benzyl-4-boronic acid)-4'-N'-(benzyl-4-ethenyl)-dipyridinium bromide chloride (p-SBBV); trans-1,2-bis-4-N-(benzyl-4-boronic acid)-4'-N'-(benzyl-4-ethenyl)dipyridinium-4-ethylene dibromide; 4-N-(benzyl-3-boronic acid)-4'-N'-(benzyl-3-ethenyl)-3 phenanthrolinium dibromide; 4,4'-N,N-bis-[benzyl-(3-methylene-4-vinyl-pyridinium bromide)-5-(boronic acid)]-dipyridinium dibromide) (m-BBVBP); 4-N-(benzyl-3-(boronic acid)-7-n-[benzyl-3-(methylene-(1-oxy-3-(oxybenzylvinyl)-propane))-5-boronic acid]-4,7-phenanthrolinium dibromide; and 4,4'-N,N-bis-[benzyl-(3-methylene-4-vinylpyridiniumbromide)-5-(boronic acid)]-4,7-phenanthrolinium dibromide.

In certain embodiments, the fluorescent molecule is a pyrene sulfonate derivative. In some embodiments, the pyrene sulfonate is selected from the structure:

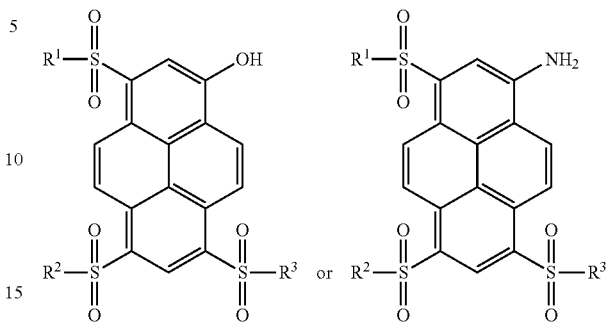

wherein $R^1$, $R^2$, and $R^3$ are each $-NHR^4$, $R^4$ is $-CH_2-CH_2(-O-CH_2-CH_2)_n-X^1$;

wherein $X^1$ is $-OH$, $OCH_3-CO_2H$, $-CONH_2$, $-SO_3H$, or $-NH_2$; and n is between 70 and 10,000.

In some embodiments, the fluorophore comprises at least one negative charge.

In some embodiments, the fluorophore is a compound formed by reacting 8-acetoxypyrene-1,3,6-trisulfonylchloride with an amino acid. In some of these embodiments, the amino acid is amino butyric acid or lysine. In certain embodiments, the fluorophore is

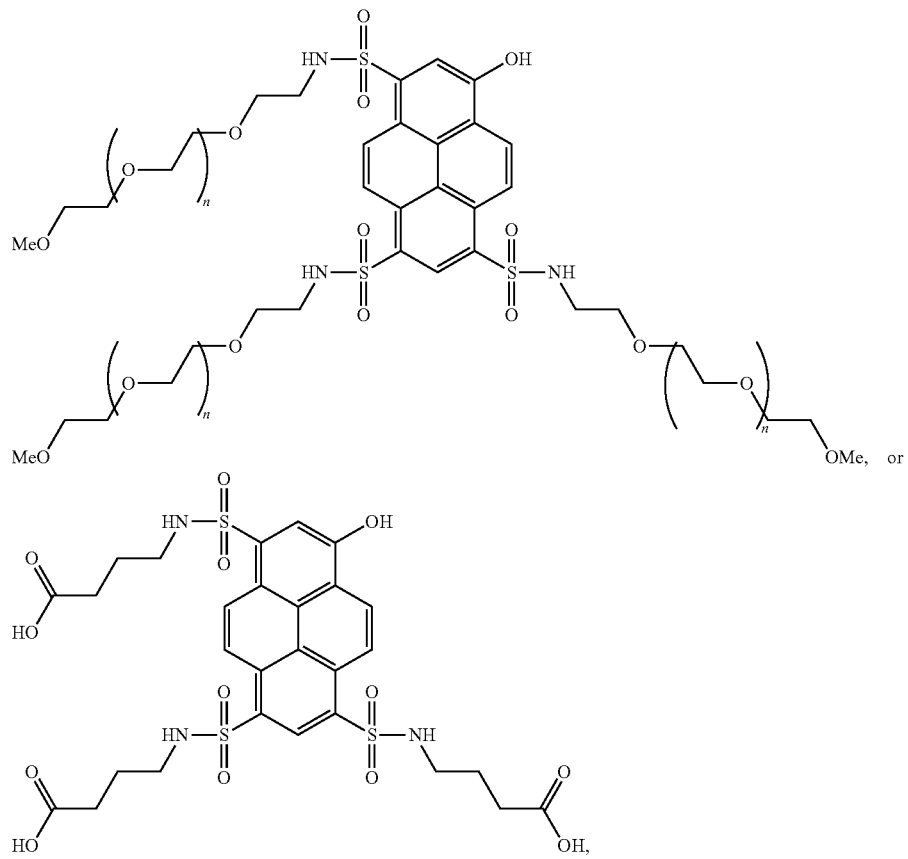

wherein n is 125.

Throughout the present disclosure, the abbreviation "HPTS" refers to 8-hydroxypyrene-1,3,6-N,N',N"-trismethoxy sulfonamide. Several derivatives of HPTS are known and are disclosed in, for example, U.S. Pat. Nos. 7,968,714, and 8,394,357, the entire disclosure of both of which is incorporated by reference herein, including the drawings, and in particular, the discussion quenchers and pyrene derivative compounds, for example those in FIGS. 1A-1C. Some derivatives of HPTS include 8-hydroxypyrene-1,3,6-N,N',N"-tris-(methoxypolyethoxyethyl (n~125) sulfonamide (HPTS-PEG); 8-acetoxypyrene-1,3,6-N,N',N"-tris-(methacrylpropylamidosulfonamide) (acetoxy-HPTS-MA); and 8-hydroxypyrene-1,3,6-N,N',N"-tris (carboxypropylsulfonamide) (HPTS-$CO_2$). A generic reference to HPTS in this disclosure can refer to any of these HPTS derivatives.

In some embodiments, the disaccharide is a synthetic disaccharide. In some of these embodiments, the disaccharide is sucralose or lactulose.

In some embodiments, the aqueous medium is a biological fluid. In some of these embodiments, the biological fluid is selected from the group consisting of blood or components thereof (e.g., serum, red cells, white cell, platelets), urine, semen, sweat, saliva, tears, and fecal matter.

In some embodiments, the subject is a mammal. In some of these embodiments, the subject is a human.

In another aspect, disclosed herein are methods of determining gastrointestinal permeability in a subject, the method comprising:

contacting an aqueous medium obtained from a subject with a system as described herein to obtain a mixture, wherein the patient has consumed a known quantity of a disaccharide;

measuring the fluorescence emission of the mixture; and correlating the extent of fluorescence emission to the concentration of the disaccharide in the aqueous medium; and correlating the concentration of the disaccharide in the aqueous medium to the gastrointestinal permeability in the subject.

In a further aspect, disclosed herein are methods of determining the concentration of a disaccharide in an aqueous medium, the method comprising:

contacting the aqueous medium comprising the disaccharide with a system as described herein to obtain a mixture;

measuring the fluorescence emission of the mixture; and correlating the extent of fluorescence emission to the concentration of the disaccharide in the aqueous medium.

Proper gastrointestinal (GI) function is critical for absorption of nutrients, a process that is facilitated by the absorptive area of the GI. The only way to noninvasively assess GI function is to perform the permeability test. Normally, human GI permeability is assessed by the measurement of urinary excretion of an orally administered disaccharide (lactulose, sucrose, or sucralose) and a monosaccharide (mannitol or L-rhamnose). The urinary excretion of these biomarkers is considered to be a parameter of gastrointestinal health. A common technique for determining the concentrations of these urinary sugars is performance liquid chromatography/mass spectrometry (LC/MS) in combination with refractive index (Ref 37). An alternative tool to using analytical instrumentation is the development of chemical assays that target the analyte of interest.

High throughput assays are becoming indispensible for studying biological processes and discovering novel compounds for potential new drug candidates. Aside from studying biological processes and discovering potent compounds, there is an increasing utility for high throughput assays in clinical chemistry. Whether it is looking for biomarkers in blood serum or urine, there are still certain assays that could be done more rapidly and effectively. One instance is a permeability test. These tests look at the gastrointestinal tract permeability to provide insight on GI barrier function. Such tests are routinely used in clinical research because of their noninvasiveness and usefulness as tools to investigate the role of increased permeability in such disorders as inflammatory bowel disease (IBD) (Crohn's disease and ulcerative colitis), Parkinson's disease, celiac disease, and diabetes mellitus, to name a few. Analysis of specific saccharide biomarkers in urine, such as lactulose, mannitol, sucrose, and sucralose, can provide this information (Ref 16-19, 36, 40). Current methods for analyzing these biomarkers require expensive and time consuming instrumentation such as high performance liquid chromatography/ mass spectrometry (LC/MS). There has been a growing interest in using specific saccharides as biomarkers (lactulose, mannitol, sucralose, and sucrose) for assessing gastrointestinal permeability. Disclosed herein are rapid and high throughput chemical assays that can quantify the concentration of more complex non-reducing saccharides, such as sucralose.

Boronic acids are known to undergo reversible covalent interactions with cis-hydroxyl functional groups, which are commonly found in saccharides. Since saccharides have multiple hydroxyl groups, it has not been fully elucidated how boronic acid receptors bind to their saccharide target. Currently the exact position on the saccharide that reacts with the boronic acid is not well understood, especially in acyclic sugar alcohols. What is understood is that boronic acids form covalent bonds with the hydroxyl groups in the cis 1,2 or 1,3 positions to form five- or six-membered rings. This does not always hold true: if this were the case, then every boronic acid receptor made would follow a similar pattern for a range of saccharides with high selectivity and sensitivity. Based on previous studies it has been shown that the saccharide target is preferably a reducing saccharide containing the hemiacetal (or hemiketal) to obtain a significant signal. Since most of the focus has been on developing sensitive and selective boronic acid receptors for glucose and fructose, although these are important saccharides, there are other saccharides such as sucralose that are not commonly studied and are becoming recognized as equally important. The biomarker sucralose can be used to noninvasively assess the colon health and potentially serve as an early indicator before the onset of colon cancer and other maladies associated with colon health.

Sucralose is among the only probes that are used for assessing colonic permeability. Typically, urine is collected from 6 to 24 hours after oral ingestion and urinary excretion is quantified as a percent of the amount ingested.

The present disclosure is directed to methods of detecting a chlorinated disaccharide (e.g., sucralose) in a solution using a two-component system that comprises a boronic acid receptor and a fluorescent molecule reporter. A diverse class of boronic acid receptors are synthesized and used in the disclosed methods to identify optimal sensitivity for saccharide biomarker lactulose.

The disaccharide sucralose is used as a commercial artificial sweetener, which is synthesized by replacing three of the hydroxyl groups on sucrose with chlorine. It is regarded to be 600 times sweeter than sucrose, but is impervious to sucrase hydrolysis (Ref 6). Since it appears in the urine unchanged, it has been utilized widely as a biomarker for measuring small intestinal and colonic permeability (Ref 6).

If small intestinal permeability is normal, then it can be used to detect an increase in colonic permeability alone. A common technique for determining the concentrations of these urinary sugars is liquid chromatography/mass spectrometry (LC/MS) in combination with refractive index (Ref 1). An alternative way to using analytical instrumentation is the development of chemical assays that target this analyte of interest.

Disclosed herein are methods to measure the concentration of sucralose via fluorescence. The primary and secondary alkyl halides of sucralose are reacted such that they are replaced by hydroxyl groups and the fructose ring is opened in order to couple sucralose to a fluorescent urine assay for gut permeability. This is possible and reliable in urine because chlororganics otherwise do not normally appear in µM concentrations in urine.

Boronic acid recognition of sucralose is better achieved by developing a degradation pathway of sucralose into a saccharide that would consist of the hydroxyl groups. The halogenated carbons can be modified via a hydroxyl anion or radical to dechlorinate sucralose, yielding a detectable sugar alcohol. Based on literature precedence, sucralose can be modified through advanced oxidation photolysis to generate a sugar alcohol derivative, which is thought to only be detectable by mass spectrometry (Ref 38). The methods described herein utilize the Fenton and similar oxidation reactions to generate reactive hydroxyl and radical species in solution to de-chlorinate sucralose to yield a sugar alcohol derivative of the fructose moiety. This modified sugar is quantified using the two component systems disclosed herein.

Further, a user-friendly platform for urinalysis assay is development and optimized, where the assay comprises ortho bis-boronic acid viologen, 4,4'-N,N'-bis-(benzyl-2-boronic acid)-dipyridinium dibromide (oBBV). Additionally, the artificial sweetener sucralose is identified using the present methods. Synthesizing a diverse class of boronic acid receptors provides a sensitive receptor for the saccharide biomarkers of interest.

Rapid quantification of saccharide biomarkers brings gastrointestinal permeability tests a step closer to routine use. This assay enables clinicians to use the permeability test routinely to monitor the GI permeability of patients who have undergone GI procedures. Such testing is of value in pharmacological studies of drug absorption and bioavailability of pharmaceuticals that affect GI permeability.

Boronic acids form covalent bonds with the cis-1, 2-hydroxyl groups that are commonly found in saccharides. Based on this property, a two-component sensing system is developed, comprising a fluorescent dye that serves as the indicator unit and a boronic acid-appended viologen that serves a dual function as fluorescence quencher and saccharide receptor. Dye and viologen form a non-fluorescent ground state complex. Binding to a diol weakens the complex. Subsequent dissociation from the fluorescent dye results in an increase in fluorescence dependent on diol concentration.

The disclosed two component system operates well by using the number and position of the boronic acid moiety, and the cationic charge number, both of which affect signal modulation. By synthesizing an array of boronic acid receptors that have unique structural and electronic properties, the present methods provide an optimal boronic acid receptor to obtain a sensitive signal for the biomarker lactulose. Overall, this system allows manipulation of the boronic receptor and the fluorescent molecule, which are tailored for detecting the saccharide of interest.

The presently disclosed methods provide cost-effective, easy-to-use platforms that are highly desirable in a clinical lab setting for the detection of chlorinated saccharide biomarkers in urine. The already synthesized oBBV, together with the dye, are deposited in the wells of a 96- or 384-well plate, or any other high throughput platform, which will require a fluorescent plate reader that is readily available in a clinical chemistry laboratory to perform an analysis. There are multiple chemical species present in human urine, the composition and concentration of which can vary depending on the subject's diet and health. An evaluation of the presently disclosed two component system (BBVs and dye) is performed to determine stability and solubility properties to obtain confident limits of detection and quantification for sucralose.

Sucralose, like sucrose, is a non-reducing compound; it is understood that boronic acids can only bind to reducing saccharides (e.g., glucose, fructose, galactose, etc). The hemiacetal (or hemiketal) group found in reducing saccharides is used in boronic acid binding. By a simple chemical transformation, sucralose is converted into a polyhydroxy product that is amenable to quantification using the oBBV receptor and dye. The presently disclosed two component system provides alternative methods to rapidly measure sucralose, alleviating the drawbacks of using expensive analytical instrumentation, such as HPLC/MS.

The design and synthesis of synthetic molecular receptors for biologically important molecules has developed into a major research area. Progress has been driven by advances in the analytical capabilities of biologists and chemists as well as from medical professionals whose practices lay increasing emphasis on accurately monitoring a patient's biochemical balance. Since the coupling of boronic acids and a fluorescent molecule by Czarnik (Ref 1) and Shinkai and co workers (Ref 2) for the detection of glucose, the field has become vastly transformed, from detecting simple monosaccharides to the recognition of cell surface carbohydrate biomarkers (Ref 3). Various research groups have developed molecular receptors for the detection of simple to complex saccharides (Ref 4, 5). Although these receptors show potential, there still remains an open avenue for the development of sensors that utilize boronic acid receptors. Over the past years, much of the focus has been on the detection of glucose, although glucose is an important analyte. There are known diagnostic saccharide biomarkers that are used noninvasively to assess gastrointestinal permeability in humans and animals in a clinical setting (Ref 6, 7). This permeability test is valuable for diagnosing primary intestinal defects. The non-invasive measurements can be exploited as a diagnostic tool to serve as an early indicator for Crohn's disease, celiac disease, irritable bowel syndrome and other gut-related or colon-related maladies, potentially before their clinical onset (Ref 8-10).

In the current standard of analysis, saccharide biomarkers are orally administered to patients and over a time interval, a urine sample is collected and analyzed by analytical instrumentation. High performance liquid chromatography is the only method for quantifying saccharide biomarkers in urine but requires a pulsed amperometric electrochemical detector or a evaporative light scatter detector (11). Although an effective instrument, it requires trained personnel; the process is labor intensive when analyzing hundreds and thousands of samples; and costly when it comes to maintenance or parts replacement.

Disclosed herein are two-component fluorescent probes that utilize a boronic acid-appended viologen (BBV) that has the dual function of a quencher and receptor, and a fluorescent molecule that generates the quantifiable signal to detect saccharides in an aqueous medium. The majority of probes that are being developed are one-component systems, which some have selectivity and sensitivity for specific saccharides. The synthesis is a difficult multistep process and there are strict limitations for modifying the parameters of the fluorophore and the receptor itself (Ref 4, 5). A two-component system is more flexible in the following sense: the fluorophore can be chosen without affecting the receptor. This research has been developed and translated for practical uses such as continuously measuring glucose levels in the blood in patients (Ref 12, 13). In the present methods, a diverse class of boronic acid receptors are developed that are specific for clinically relevant saccharide biomarkers and provide a low-cost, user-friendly high throughput platform to measure these biomarkers in urine.

The presently disclosed systems, which translate the use of boronic acid receptors to a platform that can be easily used in the permeability test to assess GI tract permeability, represent an important practical advance in patient treatment and a conceptual advance in the importance of the applicability of boronic receptors for the detection of clinically relevant saccharides. This noninvasive assay is an addition to the arsenal of diagnostics that not only help diagnose gastrointestinal disease, but also help prevent them through early detection before the onset of the disease with current treatments that are widely available (Ref 14, 15).

Synthesis of a Diverse Class of Boronic Acid Receptors to Identify Optimal Sensitivity for Saccharide Biomarker Lactulose.

Boronic acids are known to undergo reversible covalent interactions with hydroxyl functional groups, which are commonly found in saccharides. Since saccharides have multiple hydroxyl groups, it has not been fully elucidated how boronic acid receptors bind to their saccharide targets and it is not well understood what exact position on the saccharides the boronic acid reacts. What is understood is that boronic acids form covalent bonds with the hydroxyl groups in the cis 1,2 or 1,3 positions to form five or six membered rings. This does not always hold true: if this were the case, then every boronic acid receptor made should follow a similar pattern for a range of saccharides with high selectivity and sensitivity. Most of the focus has been on developing sensitive and selective boronic acid receptors for glucose and fructose, although these are important saccharides, there are other saccharides that are not commonly studied and are becoming recognized as equally important. There has been a growing interest in using specific saccharides as biomarkers (lactulose, mannitol, sucralose, and sucrose) for assessing gastrointestinal permeability (Ref 16-19). Because each saccharide is structurally diverse, the sensitive boronic receptor that has been used for glucose or fructose does not suffice. Instead, presently disclosed are methods to synthesize a diverse library of boronic acid receptors that have unique structural and electronic properties.

The presently disclosed two component system relies on a boronic acid receptor that contains a cationic charge. Formula 1 shows the general core of the boronic acid receptor that is utilized for generating a diverse class of compounds.

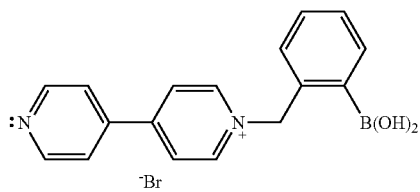

This cationic charge helps with the complex formation with the fluorophore through charge interaction and π stacking interaction (FIG. 1). The cationic charge also helps the electron acceptor capabilities of the receptor, which in turn contributes to its ability to quench the fluorescence of the fluorophore by forming a ground state complex. Because of this property, considerations for implementing multiple cationic motifs are incorporated into the synthetic strategy. The rationale for using multiple cationic charges would enhance the quenching efficacy to obtain an "off" signal. Theoretically, the more cationic character the boronic acid receptor has, the better a quencher it will be. Having multiple boronic acid units on the whole receptor increases the likelihood of interaction with the saccharide and increases the fluorescence response. Thus, in some embodiments, the boronic acids disclosed herein contain multiple cationic charges.

In addition to the compounds of Formula 1, other boronic acid compounds that are useful in the methods disclosed herein are those disclosed in, for example, U.S. Pat. Nos. 7,968,714, and 8,394,357, the entire disclosure of both of which is incorporated by reference herein, including the drawings, and in particular, the discussion on boronic acid compounds, for example, FIGS. 2A-2G and 3A-3I.

Figure 2:
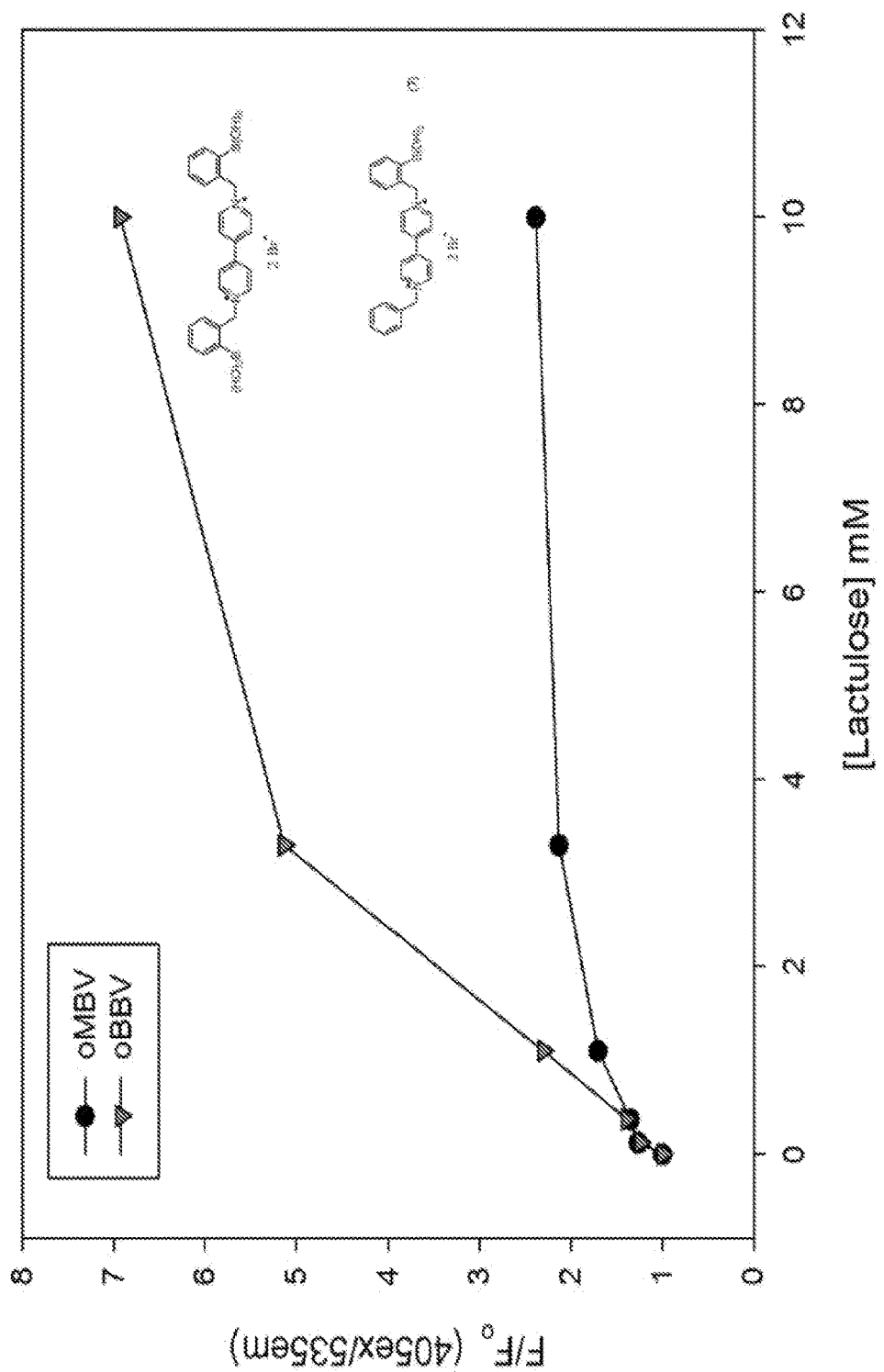
FIG. 2 is a graph showing the comparison of lactulose binding for mono vs bis substituted boronic acid viologen receptor at a ratio of 125:1 receptor to fluorophore. This study was performed with boronic acid receptor oMBV (7) and bis substituted boronic acid viologen (oBBV) in sodium phosphate buffer 0.1 M at pH 7.4. The fluorescence intensity is normalized intensity where F=fluorescence intensity after saccharide addition and $F_o$=fluorescence intensity of the quenched reporter dye.

Based on using simple, low cost starting materials that require short step syntheses for these boronic acid receptors, the synthetic approach presented herein is advantageous in developing a practical system that can be utilized by clinicians. Overall, this two-component system reduces molecular complexity, allows flexibility in multiple areas, and having stable boronic acid receptors for developing a platform is advantageous. The presently disclosed two component system is capable of detecting the saccharide biomarker lactulose. The plots in FIG. 2 illustrate a binding relationship when using the mono and bis-substituted boronic acid receptor against the disaccharide lactulose.

Boronic acids have high affinity for keto-saccharides such as fructose. Since lactulose and fructose have a ketose within their structure, similar binding affinities are expected. To the contrary, what was observed was strong binding for the acyclic sugar alcohol sorbitol and the disaccharide lactulose.

Starting with the mono-boronic acid platform, a diverse class of boronic acid receptors are synthesized to make a broad range of structurally diverse boronic acid receptors. The library is based on two structural themes: first, different receptors are synthesized that are characterized by a single unit with multiple cationic groups and are electronically unique. Second, polymeric boronic acid receptors are synthesized that comprise a water soluble peptide backbone substituted with multiple boronic acid units, the number being dictated by the length of the peptide.

The synthetic scheme for synthesizing the structurally diverse class of boronic acid receptors is outlined in Scheme 1.

Scheme 1
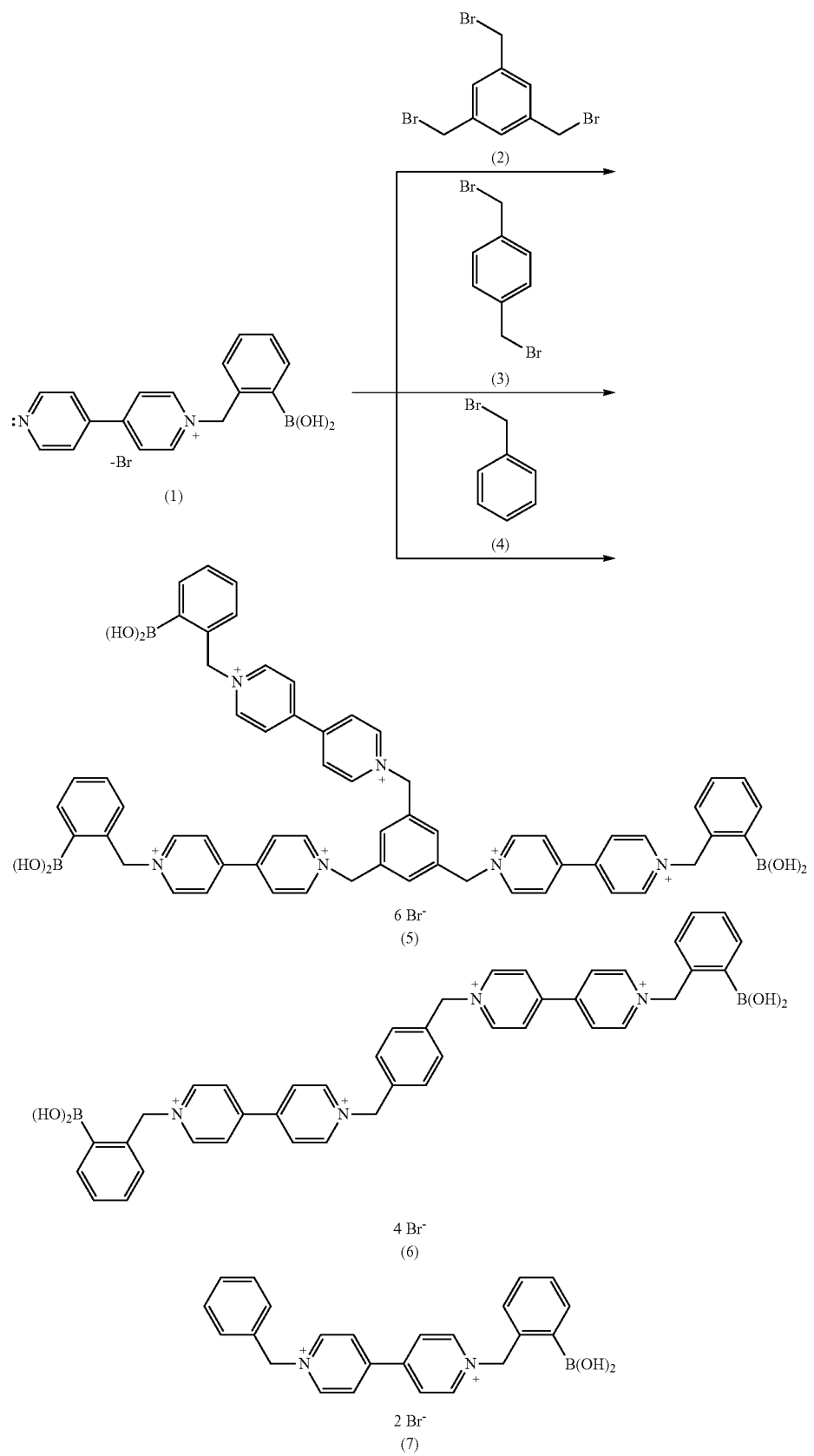

To synthesize the electronically unique receptors, the reaction scheme begins with boronic receptor 1 and three unique receptors are synthesized with the corresponding starting materials. The binding properties of Compound 7 are shown in FIG. 2. Compounds 5 and 6 are synthesized according to Scheme 1. The polymeric boronic acid receptor unit is synthesized through a similar approach. Starting with compound 1, the appropriate starting material is prepared to attach the receptor onto the polypeptide unit (Scheme 2).

ten amino acids long. The appropriate length was evaluated based on solubility and effectiveness as a receptor. The polypeptide 12 was synthesized from lysine and glycine amino acid residues through peptide-coupling synthesis. An alternative approach was to purchase commercially available poly-lysine oligomers. Compound 13 was achieved through a reductive amination or amide coupling reaction.

After the synthesis, these boronic acid receptors were tested against the saccharide biomarkers lactulose, mannitol,

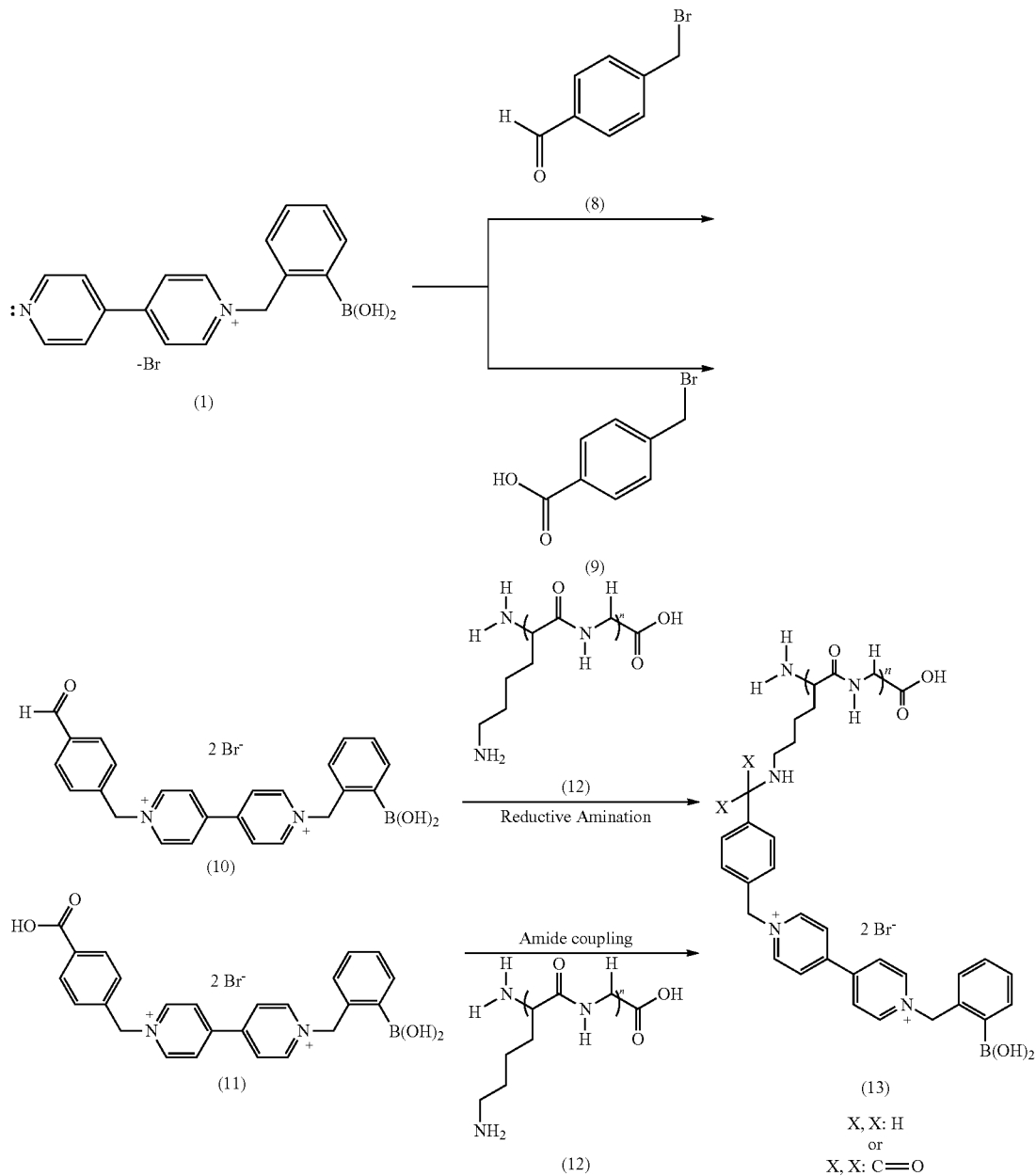

SCHEME 2

There were two routes used to achieve the above reaction; synthesis of compounds 10 and 11 were performed first, because they were the two starting reagents for the installment of the receptor onto the polypeptide unit. The polypeptide unit had an "n" repeating unit that had from five to sucrose, and sucralose to identify any structural binding relationships. Several concentrations of each saccharide were examined to determine the lower limit of detection, saturation limit, and lower limit of quantification. This was rapidly accomplished through the use of a 96-well plate and a fluorescent plate reader. Further structural elucidation was carried out via Heteronuclear Single Quantum Coherence spectroscopy (HSQC). NMR structural elucidation had been carried out for fructose and glucose thus far using phenyl boronic acid as the receptor (Ref 22, 23).

By synthesizing this diverse class of boronic acid receptors, a higher sensitivity to the lactulose biomarkers of interest was achieved. The structural features of the boronic acid receptor enhance the binding affinity for its saccharide target. Using the receptors, this binding was studied and further confirmed by indentifying structural binding relationships. Because of the multi cationic character of receptors 5 and 13, these receptors had high sensitivity for each saccharide biomarker in the targeted concentration range (50 μM-5 mM). Each receptor was demonstrated to work in various aqueous media such as human urine, phosphate buffer saline, sodium phosphate buffer, and potassium phosphate buffer at pH 7.4, proving that there were no components that can cause interference.

Development and Optimization of a User-Friendly Platform for Urinalysis Assay Comprising Ortho Bis-Boronic Acid Viologen (oBBV).

A chemical probe, in which the signaling components are dissolved in solution, is commonly used in in vitro biological assays (Ref 24, 25). Another analytical system, often more challenging to develop, is a sensor in which the probes are immobilized in polymers or on a surface. Sensors have several distinct advantages over probes. For example, sensors may cause less interference with the biological system being studied and can even be re-used for multiple experiments. Immobilization can also improve the sensitivity, as well as the selectivity, of optical probes (Ref 26). Because fabrication of sensors can be difficult, there are few examples of multi-well sensors that can be used for practical high-throughput assays (Ref 27-30). Most multi-well sensor examples in the literature make use of enzymes such as glucose oxidase to generate a signaling species. Although effective, these systems can be troublesome in different environments (high temperatures/humidity) and give inaccurate read outs at low glucose and oxygen levels. Saccharide sensors have been developed based on artificial receptors in a hydrogel matrix. These are fabricated by synthesizing polymerizable monomers of fluorescent dyes and boronic-acid containing receptors and copolymerizing them with hydrogel-forming monomers (Ref 26, 31). These sensors were designed to detect glucose in the physiological range of 1 to 20 mM. No urine assay utilizing boronic acid receptors for high throughput analysis of various saccharide biomarkers exist in the art.

In some embodiments, methyl cellulose is the immobilizing reagent that is used with preliminary boronic acid receptors. Methyl cellulose is a carbohydrate polymer that dissolves in cold water but is insoluble in hot water (reverse solubility) (Ref 33-35). It has a wide range of uses in general industrial and pharmaceutical settings. The pharmaceutical grade can be used as thickeners, binders, emulsifiers, and stabilizers. Using this reagent, various parameters, such as viscosity, concentration, and degree of polymerization of methyl cellulose are examined. In the present methods, the methylcellulose first formed a gel structure, then, upon addition of aqueous medium, the gel solid dissolved to give a clear solution. After the appropriate conditions for gel formation were achieved, the sensing elements were fixed to a substrate by entrapment in the methylcellulose gel. The fixed sensing elements were then dissolved in an aqueous saccharide solution; their ability to quantitatively analyze sugars (activation of sensing elements) was evaluated to show that the fixation did not detrimentally affect the saccharide response. Further studies are performed to determine a relative rate of dissolution, thereby achieving activation of the platform.

Other polymers instead of methyl cellulose can be used as the immobilizing regent. These include other cellulose based polymers, or other physiologically compatible polymers.

The sensing elements were then fixed onto 96-well plates and their performance was examined using the saccharide biomarkers, such as lactulose, mannitol, and sucrose, and the boronic acid receptors shown above. The stability of this platform for rapid quantification of saccharide biomarkers in human urine samples was then tested. In other studies synthetic urine media was used. Stability of the assay was examined by preparing the well plate and aging it for several days; its performance as a saccharide biomarker assay was evaluated at different time intervals. This demonstrated the feasibility for this assay to be packaged and shipped without causing any disruption to the sensing elements.

Figure 3:
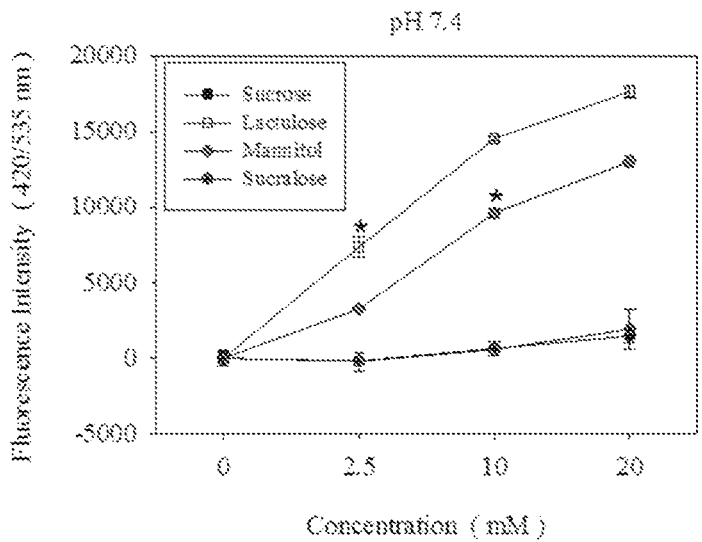
FIG. 3 is a graph showing the results of studies that demonstrate that the two component system works efficiently in human urine media.

Urine has been analyzed for the permeability markers sucrose (stomach), lactulose and mannitol (small intestine) and sucralose (colon). The viologen oBBV was used with the fluorophore HPTS (Exc. 420 or 485 nm, Em 535 nm). Fluorescence was measured with a benchtop plate reader. HPTS is normally read at 420/535 nm, but performs well at 485/535 nm, matching FITC filter sets normally found in clinical labs. The HPTS was quenched by this viologen and selectively de-quenched in the presence of the sugars lactulose and mannitol, but not sucrose or sucralose (FIG. 3). The 4,4'-o-BBV showed greatest preferential sensitivity to lactulose with good sensitivity to mannitol. Lower limit of quantification (LLOQ) and dynamic range are suitable for typical urine samples.

With equipment available to any hospital lab assistant (e.g., pipetters and plate reader), it was possible to assay more than one microtiter plate (40 patient samples in duplicate) within 30 minutes. Hence, the prototype viologen 4,4'-o-BBV offers a clear solution.

In these studies, the sensing elements are fixed onto well plates to provide a user-friendly system for clinicians. The clinician is only required to add the urine sample to the well bringing the sensing elements into solution ready for analysis. The platform comprises a specific timeline that is required for activation of sensing elements to reduce wait time. This provides a high throughput approach that allows analysis of thousands of samples within hours, making the permeability test routine. Using readily available reagents makes this platform practical at a low cost. This platform provides a faster alternative approach with the instrumentation than the conventional instrumentation.

Molecular Recognition of the Artificial Sweetener Sucralose.

The disaccharide sucralose is used as a commercial artificial sweetener, which is synthesized by replacing three of the hydroxyl groups on sucrose with chlorine. It is regarded to be as 600 times sweeter than sucrose, but makes it impervious to sucrase hydrolysis (Ref 36). Since it appears in the urine unchanged, it has been utilized widely as a biomarker for measuring small intestine and colonic permeability (Ref 36). If small intestine permeability is normal, then it can be used to detect an increase in colonic permeability alone. A common technique for determining the concentrations of these urinary sugars is performance liquid chromatography/mass spectrometry (LC/MS) in combination with refractive index (Ref 37). An alternative tool to using analytical instrumentation is the development of chemical assays that target the analyte of interest.

Figure 4:
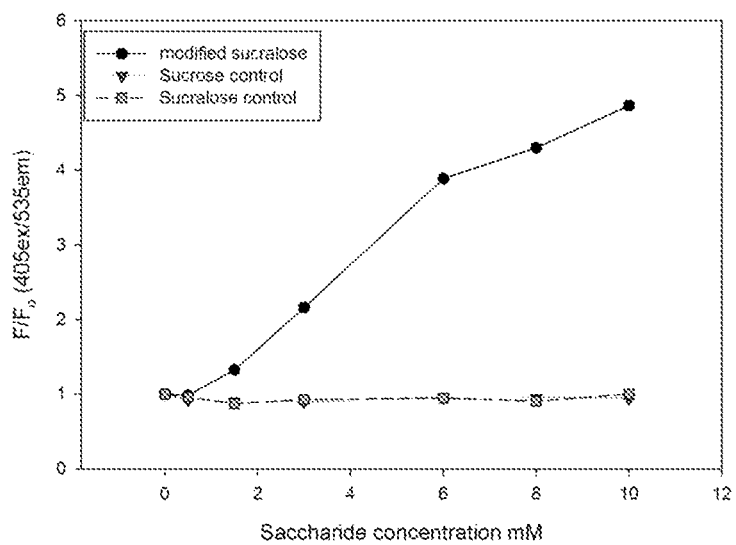
FIG. 4 is a graph showing the results of a proof of concept experiment to measure modified sucralose after 1 hr of reaction time. This study was performed with ortho bis boronic acid viologen (oBBV) in sodium phosphate and HEPES buffer 0.1M containing 0.01% Triton-X100, pH 7.4. The fluorescence intensity is the normalized intensity where F=fluorescence intensity after saccharide addition and $F_o$=fluorescence intensity of the quenched reporter dye.

Developing a degradation pathway of sucralose into a saccharide that consists of the hydroxyl groups is needed for boronic acid recognition, which allows for the molecular recognition of sucralose. Sucralose contains halogenated carbons, which are easily modified via a hydroxyl anion or radical to de-chlorinate sucralose to form a detectable saccharide. Based on literature precedence, sucralose is modified through advanced oxidation photolysis to generate a fructose sugar alcohol derivative of sucrose (Ref 38). The presently disclosed methods demonstrate that sucralose is chemically modified and measured using the disclosed oBBV-HPTS two component system. This has been accomplished by generating hydroxyl anion and radicals via the Fenton chemical reaction (Ref 39) in the presence of sucralose, and upon reaction completion, the modified sucralose solution was tested against the oBBV-HPTS system. Using the disclosed two component system, it is confirmed that sucralose is modified. By adding increasing amounts of this modified saccharide, there is an increase in fluorescence signal (FIG. 4). Sucralose and sucrose were tested in parallel with modified sucralose to show that there is no obtainable signal when attempting to measure the concentration of these non-reducing saccharides.

Thus, it has been demonstrated that sucralose can be chemically modified and measured in aqueous solution using our oBBV-HPTS two component system. This has been accomplished by generating hydroxyl anion and radicals via the Fenton chemical reaction (Ref 39) in the presence of sucralose, and upon reaction completion, the modified sucralose solution was tested against the oBBV-HPTS system. Using our two component system, we have confirmed that sucralose can be modified and measured by adding increasing amounts of this modified saccharide, a significant fluorescence signal was obtained.

Figure 5:
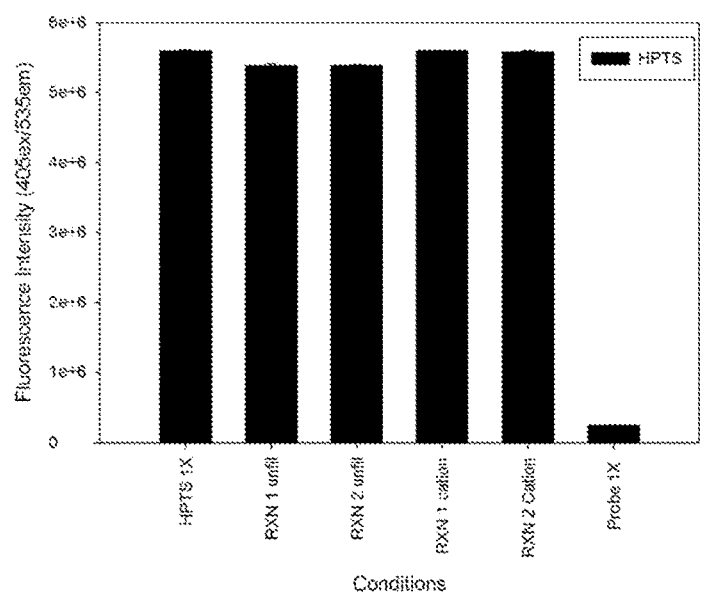
FIG. 5 is a bar graph illustrating the fluorescence obtained for various reaction conditions.

A solution of sucralose (20 mM) in the presence of ferrous iron (II) sulfate and hydrogen peroxide was allowed to stir for 1 hour and dilutions were made to determine if a fluorescence signal can be obtained. In addition, a silver nitrate test was conducted to demonstrate liberated chlorides during the reaction. The silver nitrate test gave a white precipitate, indicative of the formation silver chloride from liberated chloride ions from the Fenton oxidation of sucralose. Since iron complexes are known to form interactions with sulfonate groups, and these groups are found in our HPTS reporter dye, further analyses were performed to determine if the reaction intermediates interfere with the fluorescence signal (FIG. 5).

The conditions for the results obtained and shown in FIG. 5 were as follows: A) HPTS 1×: total fluorescence obtainable in 0.025M sodium phosphate/HEPES buffer containing 0.01% Triton-X100, pH 7.4, HPTS concentration 4 µM. RXN1 unfil: total fluorescence of HPTS in the solution after Fenton reaction went to completion without any processing (i.e. purification to remove iron complex). RXN1 conditions Sucralose (20 mM)+$H_2O_2$ (20 mM)+$FeSO_4$ (10 mM). B) RXN2 unfil: total fluorescence with conditions as mention above but with different reagent equivalences. RXN2 conditions Sucralose (20 mM)+$H_2O_2$ (40 mM)+$FeSO_4$ (10 mM). C) RXN1 and RXN2 cation is total fluorescence of HPTS in the solution after Fenton reaction went to completion and processed through a cationic exchange column to remove residual iron complexes. D) Probe 1×: Fluorescence of HPTS (4 µM) in the presence of oBBV (400 µM) in 0.025M sodium phosphate/HEPES buffer containing 0.01% Triton-X100 pH 7.4.

Based on these results, the fluorescence is slightly affected by not crudely purifying the solution after reaction has gone to completion, but is not significantly affected. By crudely purifying the solution processing the solution before analysis, the fluorescence is no longer affected by residual iron complexes. The fluorescence recovery shown in FIG. 1 is obtained after processing the solution through the cationic exchange column. This assay can be performed rapidly using a 96- or 384 well plate, which allows analysis of multiple samples per plate. This proof of principle will allow for rapid analysis of sucralose in any media (urine, buffer, plasma, serum, or wastewater), addressing unmet needs for the rapid analysis of sucralose beyond only gut permeability, such as in the food industry, environmental sciences, and basic biomedicine research.

Investigations of this newly developed method were carried out for optimization. This was accomplished by characterizing the products formed upon modification reaction using mass spectrometry and 2D-NMR. By characterizing the product(s) formed, it is shown which boronic acid receptor achieves the dynamic range that is best suited for the urinalysis assay. The presently disclosed boronic acid receptors are efficient at obtaining dynamic ranges in concentration greater than two orders of magnitude for modified sucralose.

Using the presently disclosed oBBV-HPTS system, it is possible to rapidly quantify, for the first time, the concentration of sucralose using a fluorescent 96- or 384-well platform. This method can be applied in media such as blood, serum, urine, and water. The presently disclosed system allows the analysis of multiple samples containing the biomarker sucralose to gain insight of human health depending on how it is administered (orally or intravenous injection) and can be measured in plasma, serum, or urine. In addition, an alternative modification can be applied to this system as well; the method described here uses the Fenton reaction to generate the reactive oxygen species to carry out the conversion of sucralose to sugar alcohol derivative of fructose. Alternatively, an enzymatic or photolysis approach can be utilized to generate this reactive species. This method would allow for rapid analysis of a sample containing sucralose whether it is to non-invasively assess colon health to gain early insight before the onset of colon maladies or determine concentration of it for food industry/environmental purposes.

It is self-evident that this same assay or a minor variation of its basic scheme may be employed for other purposes, such as quantifying chlorinated compounds in food or drinking water if diol groups are made available.

REFERENCES

1. Yoon J, Czarnik A W. FLUORESCENT CHEMOSENSORS OF CARBOHYDRATES—A MEANS OF CHEMICALLY COMMUNICATING THE BINDING OF POLYOLS IN WATER BASED ON CHELATION-ENHANCED QUENCHING. Journal of the American Chemical Society. 1992; 114(14):5874-5.
2. Kondo K, Shiomi Y, Saisho M, Harada T, Shinkai S. SPECIFIC COMPLEXATION OF DISACCHARIDES WITH DIPHENYL-3,3'-DIBORONIC ACID THAT CAN BE DETECTED BY CIRCULAR-DICHROISM. Tetrahedron. 1992; 48(38):8239-52.
3. Ellis G A, Palte M J, Raines R T. Boronate-Mediated Biologic Delivery. Journal of the American Chemical Society. 2012; 134(8):3631-4.
4. Jianzhang Z, James T D. Chemoselective and enantioselective fluorescent recognition of sugar alcohols by a bisboronic acid receptor. Journal of Materials Chemistry.

2005; 15(27-28):2896-901. 5. Cheng Y, Ni N, Yang W, Wang B. A New Class of Fluorescent Boronic Acids That Have Extraordinarily High Affinities for Diols in Aqueous Solution at Physiological pH. Chemistry—a European Journal. 2010; 16(45):13528-38.
6. Frias R, Steiner J M, Williams D A, Sankari S, Westermarck E. Urinary recovery of orally administered chromium 51-labeled EDTA, lactulose, rhamnose, D-xylose, 3-O-methyl-D-glucose, and sucrose in healthy adult male Beagles. American Journal of Veterinary Research. 2012; 73(5):654-8.
7. McOmber M E, Ou C-N, Shulman R J. Effects of Timing, Sex, and Age on Site-specific Gastrointestinal Permeability Testing in Children and Adults. Journal of Pediatric Gastroenterology and Nutrition. 2010; 50(3):269-75.
8. Teahon K, Smethurst P, Pearson M, Levi A J, Bjarnason I. THE EFFECT OF ELEMENTAL DIET ON INTESTINAL PERMEABILITY AND INFLAMMATION IN CROHNS-DISEASE. Gastroenterology. 1991; 101(1): 84-9.
9. Hamilton I, Cobden I, Rothwell J, Axon A T R. INTESTINAL PERMEABILITY IN CELIAC-DISEASE—THE RESPONSE TO GLUTEN WITHDRAWAL AND SINGLE-DOSE GLUTEN CHALLENGE. Gut. 1982; 23(3):202-10.
10. Bjarnason I, Macpherson A, Somaslindaram S, Teahon K. NONSTEROIDAL ANTIINFLAMMATORY DRUGS AND INFLAMMATORY BOWEL-DISEASE. Canadian Journal of Gastroenterology. 1993; 7(2):160-9.
11. Bjarnason I, Macpherson A, Hollander D. INTESTINAL PERMEABILITY—AN OVERVIEW. Gastroenterology. 1995; 108(5):1566-81.
12. Peyser T, Zisser H, Khan U, Jovanovic L, Bevier W, Romey M, Suri J, Strasma P, Tiaden S, Gamsey S. Use of a novel fluorescent glucose sensor in volunteer subjects with type 1 diabetes mellitus. J Diabetes Sci Technol. 2011; 5(3):687-93.
13. Thoniyot P, Cappuccio F E, Gamsey S, Cordes D B, Wessling R A, Singaram B. Continuous glucose sensing with fluorescent thin-film hydrogels. 2. Fiber optic sensor fabrication and in vitro testing. Diabetes Technology & Therapeutics. 2006; 8(3):279-87.
14. Webb D-L, Rudholm-Feldreich T, Gillberg L, Halim M A, Theodorsson E, Sanger G J, Campbell Calif., Boyce M, Naslund E, Hellstrom P M. The type 2 CCK/gastrin receptor antagonist YF476 acutely prevents NSAID-induced gastric ulceration while increasing iNOS expression. Naunyn Schmiedebergs Arch Pharmacol. 2013; 386 (1):41-9.
15. Hellstrom P M, Webb D L. IRRITABLE BOWEL SYNDROME—PRINCIPLES AND NOVEL TREATMENT OPTIONS. Drugs of the Future. 2011; 36(9):669-75.
16. Welcker K, Martin A, Kolle P, Siebeck M, Gross M. Increased intestinal permeability in patients with inflammatory bowel disease. Eur J Med Res. 2004; 9(10):456-60.
17. Smecuol E, Bai J C, Vazquez H, Kogan Z, Cabanne A, Niveloni S, Pedreira S, Boerr L, Maurino E, Meddings J B. Gastrointestinal permeability in celiac disease. Gastroenterology. 1997; 112(4):1129-36.
18. Dunlop S P, Hebden J, Campbell E, Naesdal J, Olbe L, Perkins A C, Spiller R C. Abnormal intestinal permeability in subgroups of diarrhea-predominant irritable bowel syndromes. American Journal of Gastroenterology. 2006; 101(6):1288-94.
19. Teahon K, Smethurst P, Levi A J, Menzies I S, Bjarnason I. INTESTINAL PERMEABILITY IN PATIENTS WITH CROHNS-DISEASE AND THEIR 1ST DEGREE RELATIVES. Gut. 1992; 33(3):320-3.
20. Wang X, Feng L, Zhang L. Reversible "off-on" fluorescent probe for anions based on a facile two-component ensemble. Dyes and Pigments. 2013; 97(2):318-23.
21. Sharrett Z, Gamsey S, Levine P, Cunningham-Bryant D, Vilozny B, Schiller A, Wessling R A, Singaram B. Boronic acid-appended bis-viologens as a new family of viologen quenchers for glucose sensing. Tetrahedron Letters. 2008; 49(2).
22. Norrild J C, Eggert H. Boronic acids as fructose sensors. Structure determination of the complexes involved using (1)J(CC) coupling constants. Journal of the Chemical Society-Perkin Transactions 2. 1996(12):2583-8.
23. Norrild J C, Eggert H. Evidence for Mono- and Bisdentate Boronate Complexes of Glucose in the Furanose Form. Application of 1JC-C Coupling Constants as a Structural Probe. J Am Chem Soc. 1995; 117(5):1479-84.
24. Anslyn E. Supramolecular analytical chemistry. The Journal of organic chemistry. 2007; 72(3):687-99.
25. Mader H S, Wolfbeis O S. Boronic acid based probes for microdetermination of saccharides and glycosylated biomolecules. Microchimica Acta. 2008; 162(1-2).
26. Yamaguchi S, Yoshimura I, Kohira T, Tamaru S-I, Hamachi I. Cooperation between artificial receptors and supramolecular hydrogels for sensing and discriminating phosphate derivatives. Journal of the American Chemical Society. 2005; 127(33):11835-41.
27. Cheng H-W, Huan S-Y, Wu H-L, Shen G-L, Yu R-Q. Surface-enhanced Raman spectroscopic detection of a bacteria biomarker using gold nanoparticle immobilized substrates. Analytical chemistry. 2009; 81 (24): 9902-12.
28. Duong H, Rhee J. Use of CdSe/ZnS core-shell quantum dots as energy transfer donors in sensing glucose. Talanta. 2007; 73(5):899-905.
29. Sarina A, Gernot T J, Christian K, Jochen G, Otto S W, Ingo K. Characterization of microtiterplates with integrated optical sensors for oxygen and pH, and their applications to enzyme activity screening, respirometry, and toxicological assays. Sensors and Actuators B: Chemical. 2006; 113.
30. Gamsey S, Suri J, Wessling R, Singaram B. Continuous glucose detection using boronic acid-substituted viologens in fluorescent hydrogels: linker effects and extension to fiber optics. Langmuir: the ACS journal of surfaces and colloids. 2006; 22(21):9067-74.
31. Suri J T, Cordes D B, Cappuccio F E, Wessling R A, Singaram B. Monosaccharide detection with 4,7-phenanthrolinium salts: Charge-induced fluorescence sensing. Langmuir. 2003; 19(12):5145-52.
32. Boaz V, Alexander S, Ritchie A W, Bakthan S. Multiwell plates loaded with fluorescent hydrogel sensors for measuring pH and glucose concentration. Journal of Materials Chemistry. 2011; 21.
33. Stewart G J, Wang Y Q, Niewiarowski S. METHYLCELLULOSE PROTECTS THE ABILITY OF ANCHORAGE-DEPENDENT CELLS TO ADHERE FOLLOWING ISOLATION AND HOLDING IN SUSPENSION. Biotechniques. 1995; 19(4):598-&.
34. Reamer R, Dey B P, Thaker N. Cryopreservation of bacterial vegetative cells used in antibiotic assay. Journal of Aoac International. 1995; 78(4):997-1001.

35. Freedman V H, Shin S. CELLULAR TUMORIGENICITY IN NUDE MICE—CORRELATION WITH CELL-GROWTH IN SEMISOLID MEDIUM. Cell. 1974; 3(4): 355-9.
36. Meddings J B, Gibbons I. Discrimination of site-specific alterations in gastrointestinal permeability in the rat. Gastroenterology. 1998; 114(1):83-92.
37. Miki K, Butler R, Moore D, Davidson G. Rapid and simultaneous quantification of rhamnose, mannitol, and lactulose in urine by HPLC for estimating intestinal permeability in pediatric practice. Clinical Chemistry. 1996; 42(1):71-5.
38. Keen O S, Dotson A D, Linden K G. Evaluation of Hydrogen Peroxide Chemical Quenching Agents following an Advanced Oxidation Process. Journal of Environmental Engineering-Asce. 2013; 139(1):137-40.
39. Lloyd R V, Hanna P M, Mason R P. The origin of the hydroxyl radical oxygen in the Fenton reaction. Free Radical Biology and Medicine. 1997; 22(5):885-8.
40. Farhadi A, Keshavarzian A, Holmes E W, Fields J, Zhang L, Banan A. Gas chromatographic method for detection of urinary sucralose: Application to the assessment of intestinal permeability. J Chromatogr B: Anal Technol Biomed Life Sci. 2003; 784(1): 145-54.

What is claimed is:

1. A method of determining the concentration of a sucralose in a sample from a subject, where the subject has been administered sucralose, the method comprising:
   dechlorinating the sucralose in a first solution comprising the sample;
   contacting the first solution comprising the dechlorinated sucralose with a boronic acid derivative and a fluorescent molecule to obtain a first mixture;
   measuring the fluorescence emission of the first mixture;
   contacting a second solution comprising a known amount of dechlorinated sucralose with the boronic acid derivative and the fluorescent molecule to obtain a second mixture;
   measuring the fluorescence emission of the second mixture and
   contacting a third solution known to contain an amount of dechlorinated sucralose too low to be detected using the boronic acid derivative and the fluorescent molecule to obtain a third mixture;
   measuring the fluorescence emission of the third mixture;
   generating a series of standards from the fluorescent emissions of the second and third mixtures; and
   comparing the fluorescence emission of the first mixture to the series of standards, thereby determining the concentration of the sucralose in the aqueous medium.

2. The method of claim 1 where the boronic acid derivative comprises 4,4'-N,N'-bis-(benzyl-2-boronic acid)-dipyridinium dibromide (oBBV).

3. The method of claim 1 where the fluorophore comprises HPTS.

4. The method of claim 1 where the sample comprises a biological fluid.

5. The method of claim 4 where the biological fluid comprises one or more of blood, or a fraction thereof, urine, semen, sweat, saliva, tears, or fecal matter.

6. The method of claim 1, further comprising collecting the sample from the subject.

7. The method of claim 1 further comprising administering the sucralose to the subject.

8. The method of claim 7 where the sucralose is administered orally.

* * * * *